United States Patent [19]

Kato

[11] 4,273,705

[45] Jun. 16, 1981

[54] METHOD FOR PREPARING COLLAGEN FILAMENTS FOR USE IN MEDICAL TREATMENTS

[75] Inventor: Tadaaki Kato, Tokyo, Japan

[73] Assignee: Kureha Kagaku Kogyo Kabushiki Kaisha, Tokyo, Japan

[21] Appl. No.: 91,343

[22] Filed: Nov. 5, 1979

[30] Foreign Application Priority Data

Oct. 4, 1979 [JP] Japan ............................ 54-128158

[51] Int. Cl.³ .................... C07G 7/00; C08H 1/06; C08L 89/06
[52] U.S. Cl. .................... 260/123.7; 424/177; 106/161
[58] Field of Search .................... 260/123.7; 106/161

[56] References Cited

U.S. PATENT DOCUMENTS

| 3,706,631 | 12/1972 | Falk | 260/112 B X |
|---|---|---|---|
| 4,204,992 | 5/1980 | Cruz, Jr. | 260/123.7 |

OTHER PUBLICATIONS

Chem. Abstracts, vol. 74, 1971, 88693q, Schaller et al.
Chem. Abstracts, vol. 79, 1973, 101808f, O'Shea et al.

Primary Examiner—Howard E. Schain
Attorney, Agent, or Firm—Wegner & Bretschneider

[57] ABSTRACT

A method for preparation of collagen filaments for use in medical treatments comprising the steps of dispersing a finely shredded insoluble collagen material from which impurities have already been removed in an aqueous acidic solution and of subjecting the thus dispersed collagen material to irradiation of ultrasonic waves.

3 Claims, No Drawings

METHOD FOR PREPARING COLLAGEN FILAMENTS FOR USE IN MEDICAL TREATMENTS

This invention relates to a method for preparing collagen filaments in which an insoluble collagen material is solubilized by the irradiation of ultrasonic waves thereon in an aqueous acidic solution.

It has been hitherto known that collagen has a high water-absorbency and has a blood-coagulating function, and collagen has been utilized as an absorbent or a hemostatic material taking advantage of these properties. The blood-coagulating function of collagen results from the reaction of collagen and thrombocytes.

The other properties of collagen such that collagen easily adheres to the surface of tissues of living things, offers scaffoldings to the growth of tissues of living things and its water-absorbency is raised to be as 100 times of its own weight after having been made more porous are suitable for its use as wound-dressing material.

Collagen is a protein constituting the tissue of cutis vera, the cartilage, ossa, the tendons, etc. of animals, and its molecule is in turn constituted by units of tropocollagen of about 2800 Å in length and about 15 Å in diameter.

Since collagen itself is originally a protein having a low antigenicity, it is utilized as a material for medical treatments. However, the inter-molecular bonding proceeds between the molecules of collagen in animal bodies with the animal's age with a result of predominance of insolubilized collagen in the animal body. Accordingly, the collagen filaments prepared from the insolubilized collagen as the raw material is not necessarily excellent in its absorption into the living body and in its adaptability to the living body.

In order to solve such a problem, a method has been hetherto adopted in which a certain proteinase is made to react with the collagen material to form soluble collagen, and by processing the thus obtained soluble collagen the material for use in medical treatments is prepared.

However, the method of solubilization of collagen by a proteinase is not necessarily advantageous from the industrial and economical point of view and further from the view point of quality according to the following facts (1) and a concern (2):

(1) The cost of the proteinase occupies a considerable portion of the production cost of the product because of the relatively high price of the purified enzyme, of the instability of the enzyme itself and of the impossiblity of re-use of the enzyme.

(2) Since it is extremely difficult to remove the enzyme completely from the solubilized collagen and the inactivation of the remaining enzyme in the solubilized collagen by heating is very difficult because of concern regarding the possible denaturation of solubilized collagen into gelatine by the heating.

It has been found in the present invention that the insoluble collagen material is solubilized by cutting the inter-molecular bondings of collagen molecules by the irradiation of ultrasonic waves onto the collagen material dispersed in an aqueous acid solution, and it is possible to obtain collagen filaments excellent in bio-adaptability, the velocity of blood-coaguration, etc. for use in the medical field, from the solubilized collagen.

According to the present invention the collagen material is at first dispersed in an aqueous acidic solution and then the disperse system is irradiated with ultrasonic waves to cut the inter-molecular bonding between the collagen molecules so that the solubilization of insoluble collagen material is performed for obtaining of collagen fiber having excellent specific properties for use in medical treatment.

In the method of the invention, when the pH of the aqueous acidic solution is higher than 4, the acidic swelling of the raw material is not sufficiently carried out, and when the pH is lower than 2, deposition of the once swollen collagen material occurs, therefore the pH higher than 4 and lower than 2 is not preferable.

On the other hand, when the amount of collagen material in the disperse system is larger than 10% by weight, the handling of the system is difficult because of the high viscosity of the system, and when it is less than 0.2% by weight, the amount of water to be removed after solubilization of collagen becomes too large to be treated economically.

As for the acid used to prepare the aqueous acidic solution, inorganic acids such as hydrochloric acid, etc. and organic acids such as acetic acid, butyric acid, etc. are effective, however, acetic acid is mainly used in view of its strong lyotropic effect on collagen.

Conditions of ultrasonic irradiation depend on the amount of the disperse system to be irradiated, the concentration of collagen in the disperse system and the capacity of the ultrasonic wave generator, however, waves in the region generally called ultrasonic may be used effectively.

On irradiation under the above-mentioned conditions, the disperse system which was at first extremely viscous and opaque becomes gradually less viscous and more translucent with the progress of the solubilization of collagen material. The thus obtained liquid treated with ultrasonic irradiation is further treated by the steps of freeze drying, neutralization, dialysis, etc. to regenerate the solubilized collagen filaments easily. The specific physical properties of the thus obtained solubilized collagen filaments resemble those of tropocollagen.

The inter-molecular bonding in the end portion of the collagen molecule is broken with the irradiation of ultrasonic waves with a result of giving monomolecular collagen filaments excellent in properties for use in medical treatments, and this fact is also confirmed by the electronmicroscopic observation of a stripped pattern having a specific period of 700 Å.

And the fact that the collagen has not been gelatinized is also confirmed by the temperature of denaturation from the thus obtained collagen filament to gelatin. That is, while the denaturation temperature from the ultrasonic wave-treated collagen according to the present invention to gelatin is around 34° C., that of the raw material, not-opened cutis vera, is 56° C., that of the mechanically opened cutis vera is 46° C. and that of solubilized collagen by the enzyme is 31° C. In other words, the collagen obtained by the method of the present invention is closely allied to the solubilized collagen by the enzyme regarded to be excellent for use in medical treatments.

Moreover, since enzymes, sodium hydroxide, sodium sulfate, etc. are not used in the method of the present invention, there are no possibilities of their residues in the product, resulting in no necessity of procedures of purification of the product from those chemicals. Also there are no possibilities of contamination by heavy metals due to the use of chemicals, resulting in the favorable quality for use in medical treatments.

In cases where the thus obtained solubilized collagen is used as a material for medical treatments, the collagen is processed by the generally utilized methods, for instance, as follows:

(1) Collagen is neutralized or dialyzed and dried to cakes of collagen. Pulverization of collagen cakes gives the collagen powder, (2) the solution containing solubilized collagen is directly freeze-dried to porous bodies, and these porous bodies may be pulverized to collagen powder, and (3) the solution containing the solubilized collagen is processed by the method of electro-deposition or casting to obtain membranes to be dried to produce collagen film, to give the respective products.

The following are the concrete explanation of the present invention by way of a non-limiting Example:

EXAMPLE:

Fourty grams (dry weight of 10 g) of a purified insoluble collagen material (Starehide, USA) cut into square platelets of 3 to 8 mm in side were soaked in 500 ml of an aqueous 0.4 M acetic acid solution for 15 hours to be acid-swollen.

The thus acid-swollen platelets of collagen material were dispersed into 2 liters of an aqueous 0.4 M acetic acid solution in a juice-mixer and after filtering the raw disperse system, a dispere system containing 0.5% by weight of collagen was formed.

On applying ultrasonic waves of 20 kHz to the disperse system for 3 hours while cooling the container from outside with ice-water, the viscosity of the system showed a gradual reduction with gradual increase of the transparency of the system as the time passed, resulting in a clear solution showing the degradation of the original collagen material by the break of intermolecular bondings. The temperature of denaturation of the thus ultrasonic wave-treated collagen to gelatin was determined to be 34° C.

Solid porous cakes obtained by freeze-drying of the above-mentioned ultrasonic wave-treated solution were subcutaneously on the back of male Donryū rats of age of 6 to 7 weeks at a rate of about 10 mg/animal and intraperitoneally into male ICR mice of age of 6 to 7 weeks at a rate of about 5 mg/animal. After 4 days of the operation, the collagen had completely disappeared by absorption as in the cases of the solubilized collagen by the enzyme. The collagen solubilized by enzyme mentioned herein is the product obtained by pretreating the collagen material with an aqueous solution containing sodium hydroxide and sodium sulfate and by solubilizing the pretreated collagen material with a proteinase (Pronase, registered trade name of Kaken Kagaku Co. Ltd.) at a pH valve of 9.

On the other hand, in the test quite similarly carried out as above, however, using the untreated collagen material, some residual collagen were observed even after a week of the operation.

In the blood-coagulation tests carried out using human platelet-rich-plasma, the time required from the addition of the specimen to the beginning of coagulation was 2'5" for the ultrasonic wave-treated collagen of the present invention and 2'26" for the solubilized collagen by the enzyme.

What is claimed is:

1. A method for preparation of collagen filaments for use in medical treatments comprising the steps of dispersing in an aqueous acidic solution a finely shredded insoluble collagen material, from which impurities have been removed without use of enzymes, alkali or heavy metals, and of subjecting the thus dispersed collagen material to irradiation of ultrasonic waves.

2. The method according to claim 1, wherein the pH of the aqueous acidic solution is 2 to 4.

3. The method according to claim 1, wherein the amount of collagen material dispersed in the aqueous acidic solution is 0.2 to 10% by weight of the solution.

* * * * *